United States Patent
Adams

Patent Number: 5,427,099
Date of Patent: Jun. 27, 1995

[54] MARKER FOR MAGNETIC RESONANCE IMAGING

[76] Inventor: Timothy L. Adams, 1129 E. Cochise Dr., Ste. 2B, Phoenix, Ariz. 85020

[21] Appl. No.: 214,646

[22] Filed: Mar. 17, 1994

[51] Int. Cl.$^6$ ............................................. A61B 5/055
[52] U.S. Cl. .............................. 128/653.1; 128/653.2; 378/163
[58] Field of Search ............ 128/653.1, 653.4, 653.5, 128/653.2; 600/7, 8; 606/130; 424/9; 378/205, 163; 356/247-248

[56] References Cited

U.S. PATENT DOCUMENTS

| | | | |
|---|---|---|---|
| 4,187,423 | 2/1978 | Ehrhardt | 378/205 X |
| 4,506,676 | 3/1985 | Duska | 128/653.1 |
| 4,583,538 | 4/1986 | Onik et al. | 128/653.1 X |
| 4,597,961 | 7/1986 | Etscorn | 424/28 |
| 5,030,195 | 7/1991 | Nardi | 600/8 X |
| 5,052,035 | 9/1991 | Krupnick | 378/205 X |
| 5,193,106 | 3/1993 | DeSena | 378/205 X |
| 5,227,727 | 7/1993 | Segawa et al. | 324/318 |

*Primary Examiner*—Lee S. Cohen
*Assistant Examiner*—Brian L. Caster
*Attorney, Agent, or Firm*—Jordan M. Meschkow; Lowell W. Gresham

[57] ABSTRACT

A marker for magnetic resonance imaging which has two sheets of flexible plastic, a lipid sealed between the sheets of plastic, and a layer of adhesive material affixed to one of the sheets of plastic on the opposite side from the lipid.

12 Claims, 1 Drawing Sheet

MARKER FOR MAGNETIC RESONANCE IMAGING

BACKGROUND OF THE INVENTION

1. Field of the Invention

This invention relates to magnetic resonance imaging.

More particularly the present invention relates to examination of a specific area of anatomy by magnetic resonance imaging.

In a further and more specific aspect, the instant invention concerns marking the specific area to be examined.

2. Prior Art

The use of magnetic resonance imaging is well known as a noninvasive diagnostic tool for medical practitioners. Magnetic resonance images depict the interaction of body tissues with radio waves in a magnetic field. These interactions appear as dark and light areas on the images depending on the intensity of the signal produced. The difference in the intensities can be manipulated, to some extent, by adjusting the magnetic resonance imaging parameters. Bone and water cause an absence of signal making this technique very usefully in the diagnoses of soft tissue problems.

During a magnetic resonance imaging scan, large areas of the anatomy are usually examined and many areas can appear similar, for example discs in the back. This is fine if large regions are to be examined but makes it difficult to locate small specific sites. This inability to focus on the exact area of concern causes much frustration and possible inaccuracies in diagnose. To overcome this problem some way of indicating specific areas must be used.

One way of indicating the specific area to be examined is by using gadopentetate dimeglumine. This compound is injected into the bloodstream, working similar to iodine compounds in x-ray analysis, and shows up with good intensity in magnetic resonance imaging. Unfortunately, gadopentetate dimeglumine is considered to be a hazardous chemical and therefore, must be stored, handled and disposed of correctly and carefully. Also, because it is an injection it can only be used for very specific purposes, can be painful to the patient and is extremely expensive.

Another way of indicating the area of concern is to use a vitamin E capsule. Though it is easily disposed of, virtually painless to the patient, and inexpensive, it is not easy to use or to view. The capsule has a tendency to move off of the specific site unless it is some how attached to the patient, this is usually done by adhesive tape. Also, the small size of the capsule makes it hard to identify over the large areas scanned. Finally, vitamin E does not show up with much intensity on most magnetic resonance imaging scans making it almost impossible to identify.

It would be highly advantageous, therefore, to remedy the foregoing and other deficiencies inherent in the prior art.

Accordingly, it is an object of the present invention to provide a marker for magnetic resonance imaging which is easy to use.

Another object of the invention is the provision of a marker for magnetic resonance imaging which is safe and painless to the patient.

And another object of the invention is to provide a marker for magnetic resonance imaging which is economical.

Still another object of this invention is the provision of a marker for magnetic resonance imaging which is hypo-allergenic.

Yet another object of the invention is to provide a marker for magnetic resonance imaging which is disposable.

Yet still another object of the immediate invention is the provision of a marker for magnetic resonance imaging which complies with OSHA standards and FDA criteria.

And a further object of the invention is to provide a marker for magnetic resonance imaging which is pliable as well as durable, thereby being able to withstand the pressure of a human body while not causing discomfort when being laid upon for prolonged periods of time.

Still a further object of the invention is the provision of a marker for magnetic resonance imaging which does not obstruct the area to be imaged.

And still another object of the invention is to provide a marker for magnetic resonance imaging which can be seen on more images due to the size, configuration, and composition.

Yet still a further object of the invention is the provision of a marker for magnetic resonance imaging which makes it easy to locate an area of specific concern allowing for a narrower focus in the magnetic resonance imaging.

SUMMARY OF THE INVENTION

Briefly, to achieve the desired objects of the invention in accordance with the preferred embodiments thereof, provided is a marker for magnetic resonance imaging including two sheets of flexible plastic, a lipid sealed between the sheets of plastic, and a layer of adhesive material affixed to one of the sheets of plastic on the opposite side from the lipid.

More specifically, in a first embodiment of the invention, the lipid is selected from a group consisting of mineral oils, vegetable oils, and fish oils.

In a further embodiment of the invention, a method is provided for using a marker which includes the steps of locating an area of specific concern for examination by magnetic resonance imaging, affixing the marker on skin at the area to be examined, focusing on the marker, and scanning the area of concern.

BRIEF DESCRIPTION OF THE DRAWINGS

The foregoing and further and more specific objects and advantages of the instant invention will become readily apparent to those skilled in the art from the following detailed description of the preferred embodiment thereof taken in conjunction with the drawings in which.

DETAILED DESCRIPTION OF THE PREFERRED EMBODIMENT

Figure 1:
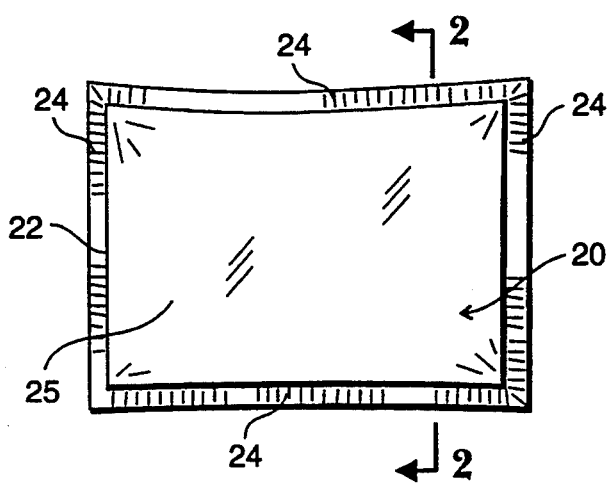
FIG. 1 is a top plan view of a marker for magnetic resonance imaging, in accordance with the instant invention.
Figure 2:
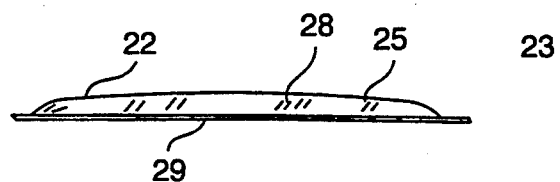
FIG. 2 is a cross-sectional view as seen from line 2—2 of FIG. 1.

Turning now to the drawings, in which like reference characters indicate corresponding elements throughout the several views, attention is first directed to FIG. 1 and 2 which illustrates a marker 20 for magnetic resonance imaging, in accordance with the instant invention. In this embodiment, marker 20 has the approximate dimensions of 2.5 inches in length by 1 inch in width by 0.5 inches in height, but it should be understood by those skilled in the art that marker 20 may be smaller or larger than these listed measurement. Marker 20 includes two sheets of flexible plastic 22 and 23, which are non-metallic and hypo-allergenic (do not cause skin sensitivity). Plastic sheets 22 and 23 are sealed on all four sides by seams 24 to form a completely encased cavity. Heat sealing, or the like, is used to form seams 24 of plastic sheets 22 and 23. Seams 24 are approximately 0.25 to 0.75 inches in width, so they can withstand the pressure exerted by a patient's body when resting on marker 20 without seams 24 splitting.

Marker 20 also includes a lipid 25 encased in the cavity of plastic sheets 22 and 23 between seams 24. Lipid 25 forms a globule 28 in marker 20, which is not more than 0.5 inches in height, as illustrated in FIG. 2. The globule is formed by using approximately 1.0 to 1.5 milliliters of lipid 25. Lipid 25 is a substance which is insoluble in water, soluble in organic or non-polar solvents, contains a long chain hydrocarbon group in the molecule, and is present or derived from living organisms. Therefore, lipid 25 includes all long chain hydrocarbons, alcohols, aldehydes, fatty acids, and their derivatives, such as glycerides, wax esters, phospholipids, glycolipids, and sulfolipides. In this embodiment, lipid 25 is selected from a group consisting of mineral oil, vegetable oils, and fish oils. Sources of these oils include, but are not limited to, coconut, corn, cottonseed, linseed, kanola, olive, palm, palm kernel, rapeseed, peanut, safflower, soybean, sunflower, capelin, cod liver, cuttlefish, herring, menhaden, pollack, salmon, sardine, shark, shrimp, short-neck clam, skipjack, and squid.

Figure 3:
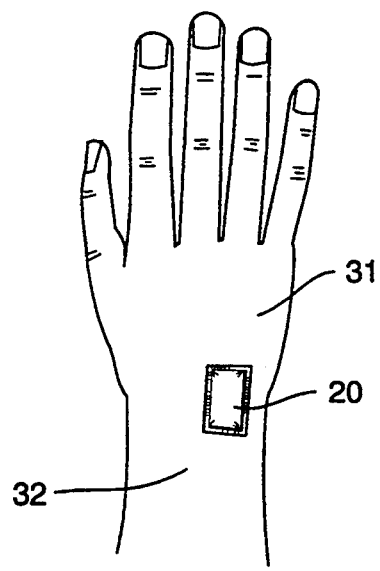
FIG. 3 is a top plan view of the marker affixed to a wrist.

Marker 20 has a layer of adhesive material 29 affixed to the side opposite from lipid 25 of plastic sheet 23, as illustrated in FIG. 2. Adhesive material 29 is clear and hypo-allergenic with a peel-off backing. Adhesive layer 29 is used to affix marker 20 to skin 31 of the patient, as illustrated in FIG. 3.

A first step in using marker 20 is to locate an area of specific concern for examination by magnetic resonance imaging. Some areas marker 20 may be used on, include, cancerous growths, slipped discs, torn muscles, torn ligaments, torn cartilage, abnormal tissues, hematomas, cysts, multiple sclerosis, carpal tunnel, and masses. The next step is to remove the backing from adhesive material 29 and affix marker 20 to skin 31 in the area of concern, as illustrated in FIG. 3 on wrist 32. Marker 20 produces an intense white circle on the magnetic resonance image which can be used as a focusing point for the magnetic resonance imaging scans. This makes it easier to locate the area of concern, allowing for a narrower focus in the magnetic resonance imaging. After focusing on marker 20, the area to be examined is scanned by magnetic resonance imaging. Finally, after the scanning has been completed marker 20 is removed and discarded.

It can be seen from the above description, that the instant invention provides a marker for magnetic resonance imaging which is easy to use, economical, and safe and painless to the patient. Also, marker 20 is hypo-allergenic and disposable, complying with OSHA standards and FDA criteria. Marker 20 is pliable as well as durable, thereby being able to withstand the pressure of a human body while not causing discomfort when being laid upon for prolonged periods of time. The instant invention, also, provides a marker for magnetic resonance imaging which can be seen on most images due to the size, configuration, and composition, yet does not obstruct the area to be imaged. This makes it easy to locate an area of specific concern, allowing for a narrower focus in the magnetic resonance imaging.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A method of using a marker for magnetic resonance imaging comprising the steps of:
    providing a marker for magnetic resonance imaging comprising two sheets of flexible plastic, a lipid encased between the sheets of plastic, and a layer of adhesive material affixed to one of said sheets of plastic on the outside of said marker;
    locating an area of specific concern for examination by magnetic resonance imaging;
    affixing the marker on skin at the area to be examined by the adhesive material;
    focusing on the marker;
    scanning the area of concern with a magnetic resonance imaging device; and
    removing and disposing of the marker.

2. A method as claimed in claim 1 wherein the step of providing a marker includes selecting two sheets of flexible plastic which are non-metallic.

3. A method as claimed in claim 1 wherein the step of providing a marker includes two sheets of flexible plastic which are hypo-allergenic.

4. A method as claimed in claim 1 wherein the step of providing a marker includes selecting the lipid from the group consisting of mineral oils, vegetable oils, and fish oils.

5. A method as claimed in claim 4 wherein the step of providing a marker includes selecting the lipid to include coconut oil.

6. A method as claimed in claim 1 wherein the step of providing a marker includes selecting the adhesive material to be hypo-allergenic.

7. A method as claimed in claim 6 wherein the step of providing a marker includes providing the adhesive material with a peel off backing.

8. A method as claimed in claim 7 wherein the step of affixing the marker on skin includes removing the backing from the adhesive.

9. A method of using a marker for magnetic resonance imaging comprising the steps of:
    providing a marker for magnetic resonance imaging comprising two sheets of flexible plastic, and a lipid encased between the sheets of plastic wherein the marker is approximately 2.5 inches in length by 1 inch in width by 0.5 inches in height;
    locating an area of specific concern for examination by magnetic resonance imaging;
    affixing the marker on skin at the area to be examined;
    focusing on the marker;

scanning the area of concern with a magnetic resonance imaging device; and
removing and disposing of the marker.

10. A method as claimed in claim 9 wherein the step of providing a marker includes selecting two sheets of flexible plastic which are non-metallic and hypo-allergenic.

11. A method as claimed in claim 9 wherein the step of providing a marker includes selecting the lipid from the group consisting of mineral oils, vegetable oils, and fish oils.

12. A method as claimed in claim 11 wherein the step of providing a marker includes selecting the lipid to include coconut oil.

* * * * *